(12) United States Patent
Meens

(10) Patent No.: US 8,083,761 B2
(45) Date of Patent: Dec. 27, 2011

(54) BALLOON CATHETER AND METHOD FOR MANUFACTURING IT

(75) Inventor: Hendrik Jozef Maria Meens, Weert (NL)

(73) Assignee: C.R. Bard, Inc., Murray Hill, NJ (US)

( * ) Notice: Subject to any disclaimer, the term of this patent is extended or adjusted under 35 U.S.C. 154(b) by 1439 days.

(21) Appl. No.: 10/140,524

(22) Filed: May 7, 2002

(65) Prior Publication Data

US 2003/0014070 A1 Jan. 16, 2003

(30) Foreign Application Priority Data

May 8, 2001 (NL) .................................... 1018018

(51) Int. Cl.
*A61M 29/00* (2006.01)
(52) U.S. Cl. ........................................ 606/194; 606/192
(58) Field of Classification Search ................ 606/108, 606/191, 194, 198, 195, 192; 604/96.01, 604/103.06–103.15; 623/1.11
See application file for complete search history.

(56) References Cited

U.S. PATENT DOCUMENTS

| | | | |
|---|---|---|---|
| 4,251,305 A | 2/1981 | Becker et al. | |
| 4,511,354 A | 4/1985 | Sterling | |
| 4,762,130 A | 8/1988 | Fogarty et al. | |
| 4,946,464 A | 8/1990 | Pevsner | |
| 4,958,634 A | 9/1990 | Jang | |
| 4,963,313 A | 10/1990 | Noddin et al. | |
| 4,964,853 A | 10/1990 | Sugiyama et al. | |
| 4,994,072 A | 2/1991 | Bhate et al. | |
| 5,019,042 A | 5/1991 | Sahota | |
| 5,024,668 A | 6/1991 | Peters et al. | |
| 5,066,298 A | 11/1991 | Hess | |
| 5,087,246 A | 2/1992 | Smith | |
| 5,090,958 A | 2/1992 | Sahota | |
| 5,147,302 A | 9/1992 | Euteneuer et al. | |
| 5,160,321 A | 11/1992 | Sahota | |
| 5,192,296 A | 3/1993 | Bhate et al. | |
| 5,286,259 A | 2/1994 | Ganguly et al. | |
| 5,295,959 A | 3/1994 | Gurbel et al. | 604/96 |
| 5,304,340 A | 4/1994 | Downey | |
| 5,330,428 A | 7/1994 | Wang et al. | |
| 5,352,199 A | 10/1994 | Tower | 604/96 |
| 5,478,319 A | 12/1995 | Campbell et al. | |
| 5,484,411 A | 1/1996 | Inderbitzen et al. | |
| 5,545,132 A * | 8/1996 | Fagan et al. | 604/103.08 |
| 5,628,754 A * | 5/1997 | Shevlin et al. | 623/1.11 |
| 5,653,689 A | 8/1997 | Buelna et al. | |
| 5,714,110 A | 2/1998 | Wang et al. | |
| 5,746,745 A | 5/1998 | Abele et al. | |
| 5,800,393 A | 9/1998 | Sahota | |
| 5,891,386 A | 4/1999 | Deitermann et al. | 264/526 |
| 5,913,871 A * | 6/1999 | Werneth et al. | 623/1.11 |

(Continued)

FOREIGN PATENT DOCUMENTS

EP 0 713 712 A1 5/1996

(Continued)

*Primary Examiner* — Tuan Nguyen
(74) *Attorney, Agent, or Firm* — King & Schickli, PLLC

(57) ABSTRACT

A balloon catheter includes a catheter tube and an inflatable balloon. The ends of the balloon are attached to the catheter tube. The outside surface of the balloon in an uninflated state is provided with a relief structure which in an inflated state of the balloon is substantially disappeared. A method for producing such a relief structure is by winding a wire helically around the outer surface of the balloon.

13 Claims, 1 Drawing Sheet

U.S. PATENT DOCUMENTS

| | | | |
|---|---|---|---|
| 5,935,135 A | 8/1999 | Bramfitt et al. | |
| 5,954,740 A | 9/1999 | Ravenscroft et al. | |
| 5,976,106 A | 11/1999 | Verin et al. | |
| 6,022,359 A | 2/2000 | Frantzen | |
| 6,063,092 A * | 5/2000 | Shin | 606/108 |
| 6,106,485 A | 8/2000 | McMahon | |
| 6,110,180 A | 8/2000 | Foreman et al. | |
| 6,110,192 A | 8/2000 | Ravenscroft et al. | |
| 6,120,477 A | 9/2000 | Campbell et al. | |
| 6,129,706 A * | 10/2000 | Janacek | 604/103.08 |
| 6,168,617 B1 | 1/2001 | Blaeser et al. | |
| 6,238,412 B1 | 5/2001 | Dubrul et al. | |
| 6,258,099 B1 | 7/2001 | Mareiro et al. | |
| 6,263,248 B1 | 7/2001 | Farley et al. | |
| 6,293,959 B1 | 9/2001 | Miller et al. | |
| 6,309,402 B1 | 10/2001 | Jendersee et al. | |
| 6,346,092 B1 | 2/2002 | Leschinsky | |
| 6,364,900 B1 | 4/2002 | Heuser | |
| 6,379,369 B1 | 4/2002 | Abrams et al. | |
| 6,387,118 B1 | 5/2002 | Hanson | |
| 6,428,506 B1 | 8/2002 | Simhambhatla et al. | |
| 6,468,243 B1 * | 10/2002 | Miyagawa et al. | 604/96.01 |
| 6,478,807 B1 * | 11/2002 | Foreman et al. | 606/194 |
| 6,500,185 B1 | 12/2002 | Mathews et al. | |
| 6,520,933 B1 | 2/2003 | Evans et al. | |
| 6,524,275 B1 | 2/2003 | Lynch et al. | |
| 6,533,753 B1 | 3/2003 | Haarstad et al. | |
| 6,572,644 B1 | 6/2003 | Moein | |
| 6,572,813 B1 | 6/2003 | Zhang et al. | |
| 6,620,128 B1 | 9/2003 | Simhambhatla | |
| 6,652,485 B1 * | 11/2003 | Gaudoin et al. | 604/103.07 |
| 6,663,646 B1 | 12/2003 | Shah | |
| 6,669,680 B1 | 12/2003 | Macoviak et al. | |
| 6,786,889 B1 | 9/2004 | Musbach et al. | |
| 6,852,097 B1 | 2/2005 | Fulton, III | |
| 7,004,963 B2 * | 2/2006 | Wang et al. | 623/1.11 |
| 7,083,639 B2 * | 8/2006 | Guinan et al. | 623/1.1 |
| 2001/0022415 A1 | 9/2001 | Laksin | |
| 2001/0039395 A1 | 11/2001 | Mareiro et al. | |
| 2002/0007204 A1 | 1/2002 | Goode | |
| 2002/0013601 A1 | 1/2002 | Nobles et al. | |
| 2002/0058954 A1 | 5/2002 | Burke et al. | |
| 2002/0082634 A1 | 6/2002 | Kammerer et al. | |
| 2002/0082635 A1 | 6/2002 | Kammerer et al. | |
| 2002/0087165 A1 | 7/2002 | Lee et al. | |
| 2002/0091406 A1 | 7/2002 | Bonutti | |
| 2002/0103455 A1 | 8/2002 | Zhang et al. | |
| 2002/0111582 A1 | 8/2002 | Boussignac | |
| 2002/0150707 A1 | 10/2002 | Wilkins | |
| 2002/0151924 A1 | 10/2002 | Shiber | |
| 2002/0156494 A1 | 10/2002 | Simhambhatla et al. | |
| 2003/0055378 A1 | 3/2003 | Wang et al. | |
| 2003/0055482 A1 | 3/2003 | Schwager et al. | |
| 2003/0083687 A1 | 5/2003 | Pallazza | |
| 2003/0163148 A1 | 8/2003 | Wang et al. | |
| 2003/0163157 A1 | 8/2003 | McMorrow et al. | |
| 2003/0167067 A1 | 9/2003 | Wang et al. | |
| 2003/0171799 A1 | 9/2003 | Lee et al. | |
| 2003/0187492 A1 | 10/2003 | McHale | |
| 2003/0195382 A1 | 10/2003 | Barbut | |
| 2003/0229307 A1 | 12/2003 | Muni et al. | |
| 2004/0039410 A1 | 2/2004 | Ren | |
| 2004/0044309 A1 | 3/2004 | Owens et al. | |
| 2004/0215227 A1 | 10/2004 | McMorrow et al. | |
| 2004/0260379 A1 | 12/2004 | Jagger et al. | |
| 2004/0267195 A1 | 12/2004 | Currlin | |
| 2005/0043679 A1 | 2/2005 | Devens, Jr. et al. | |
| 2005/0113857 A1 | 5/2005 | Nohilly et al. | |
| 2005/0148997 A1 | 7/2005 | Valley et al. | |
| 2005/0151304 A1 | 7/2005 | Boelens et al. | |
| 2005/0177130 A1 | 8/2005 | Konstantino et al. | |
| 2005/0197531 A1 | 9/2005 | Cabiri et al. | |
| 2005/0228417 A1 | 10/2005 | Teitelbaum et al. | |
| 2005/0251194 A1 | 11/2005 | McHale | |

FOREIGN PATENT DOCUMENTS

| | | |
|---|---|---|
| EP | 0 737 488 A1 | 10/1996 |
| EP | 1 008 363 A2 | 6/2000 |
| EP | 1 008 363 A3 | 7/2000 |
| FR | 2753907 | 4/1998 |
| JP | 05-038367 | 2/1993 |
| JP | 08-164210 | 6/1996 |

* cited by examiner

BALLOON CATHETER AND METHOD FOR MANUFACTURING IT

TECHNICAL FIELD

The present invention relates to a balloon catheter comprising a catheter tube and an inflatable balloon which at its ends is attached to the catheter tube. The invention further relates to a method of manufacturing a balloon catheter.

BACKGROUND INFORMATION

Balloon catheters of this type are generally known and are used for dilating vessels and lumina. In order to pass the balloon catheter easily and safely through the vessels and lumina and to position it at the required place for dilatation, it is important that the balloon catheter has a small profile and is sufficiently flexible.

The object of the invention is therefore to provide an improved balloon catheter.

BRIEF SUMMARY OF THE INVENTION

The balloon catheter according to the invention is characterized in that the outside surface of the balloon in an uninflated state is provided with a relief structure which in an inflated state of the balloon is substantially disappeared.

Tests have shown that with a relief structure on the outside surface of the balloon, a catheter is obtained that is more flexible than a standard balloon catheter. The balloon catheter according to the invention can therefore be passed more easily and more safely through vessels and lumina to the point of dilatation. Because of its flexibility, the catheter will be able to adapt better to a bend in a vessel or a lumen, thus reducing the risk of damage to the vessel or lumen.

The required relief structure may have different embodiments, but preferably comprises at least one groove that extends at least transversely in the longitudinal direction of the balloon in order to give the catheter the required flexibility in a direction transverse to the longitudinal direction thereof.

The groove preferably extends at a predetermined angle with respect to the longitudinal direction of the balloon. According to a preferred embodiment the groove extends helically from one end to the other end of the balloon, over the outside surface thereof.

According to another embodiment, the relief structure comprises two or more grooves that extend helically from one end to the other end of the balloon, crossing each other. Tests have shown that with such a relief structure a very flexible balloon catheter is obtained which also has a relatively small profile.

The invention also relates to a method for producing a balloon catheter comprising attaching the ends of an inflatable balloon to a catheter tube, whereby according to the invention the outside surface of the balloon is provided with a relief structure.

According to an embodiment of the invention, the relief structure is produced on the application of heat in order to deform the elastic material of the balloon.

The relief structure is also preferably produced on the surface of the balloon by applying a high pressure to the inside of the balloon.

According to a very inexpensive method, the relief structure is produced on the surface of the balloon by winding a wire around the balloon in the form of a helix.

According to another simple method, the relief structure is produced on the surface of the balloon by taking up the balloon in a counter-pressure body that has the relief structure.

BRIEF DESCRIPTION OF THE DRAWINGS

The invention is explained in more detail on the basis of the drawings attached. The drawings show.

DETAILED DESCRIPTION OF THE INVENTION

A balloon catheter according to the invention comprises a catheter tube 1 and an inflatable balloon 2, which at its ends is attached to the catheter tube 1. In an uninflated state (FIGS. 1A and 2A), the outside surface of balloon 2 has a relief structure 4 that in the inflated state has virtually or completely disappeared (FIGS. 1B and 2B). The relief structure gives the catheter its required flexibility.

Figure 1A:
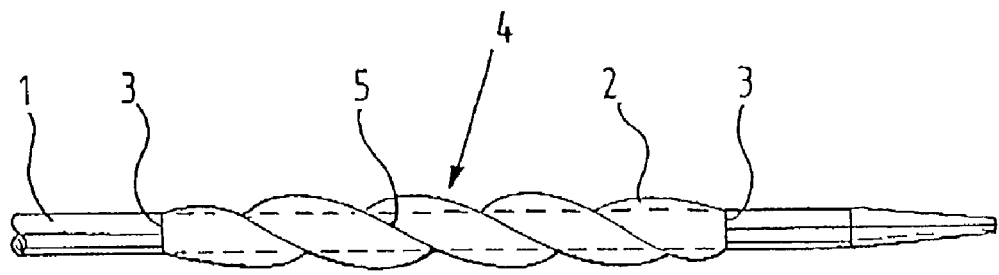
FIG. 1A is a side view of a first embodiment of a balloon catheter in an uninflated state.
Figure 1B:
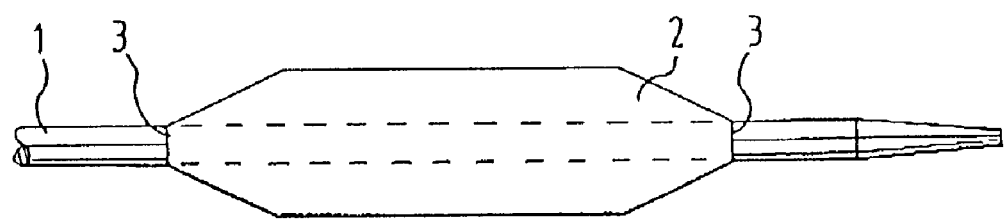
FIG. 1B is a side view of the catheter in FIG. 1A in an inflated state.

In the first embodiment according to FIGS. 1A and 1B, the relief structure 4 consists of one groove 5, which extends helically from one end 3 to the other end 3 of the balloon 2, over the outside surface thereof. The uninflated balloon 2 has thereby obtained a helical relief surface. In the second embodiment according to FIGS. 2A and 2B, the relief structure 4 consists of two grooves 5, 6, which extend helically from one end 3 to the other end 3 of the balloon 2 and thereby cross each other. The uninflated balloon 2 has hereby obtained a padded relief surface.

Other relief structures are of course possible, provided that the relief structure on the catheter creates the necessary flexibility in a direction transverse to the longitudinal direction of the balloon.

Figure 2A:
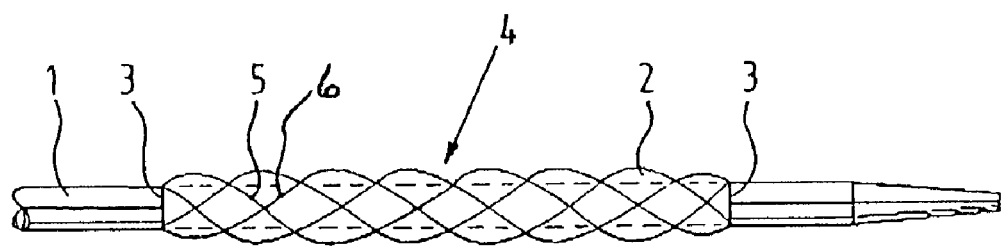
FIG. 2A is a side view of a second embodiment of a balloon catheter in an uninflated state.
Figure 2B:
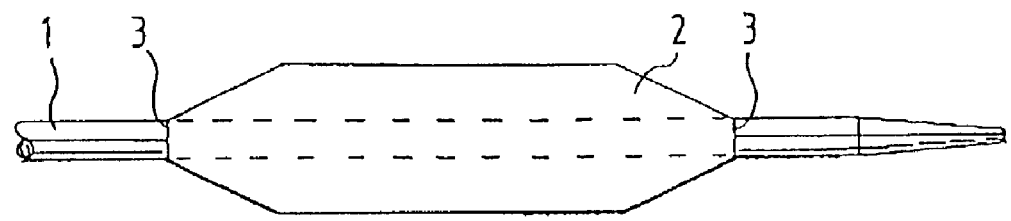
FIG. 2B is a side view of the catheter of FIG. 2A in an inflated state.

One way of obtaining the relief structure as shown in the drawings is by winding a wire helically around the balloon 2. If the wire is wound only in the forward direction, the structure according to FIG. 1A is obtained, and if the wire is also wound in the return direction, the structure in FIG. 2A is obtained. After the wire has been wound around the balloon, a sleeve is pulled over the balloon. Subsequently, with the application of raised pressure to the inside of the balloon, the balloon is heated in such a way that, in an uninflated state, the balloon obtains a relief structure that on dilating of the balloon at the dilatation site in the vessel or lumen will virtually or completely disappear. The sleeve is then removed and the balloon catheter can be inserted into a vessel or a lumen.

Instead of winding a wire, the balloon may be placed in a mould, which is provided with the relief pattern required in order for it to obtain, under raised pressure and temperature, the relief structure required.

Before the balloon is provided with its relief structure, preferably it is folded in the usual way in order to reduce its profile. By applying the relief structure, the profile will be reduced still further as an additional, advantageous effect.

The usual way of folding a balloon mounted on a catheter involves the folding of the uninflated balloon wall so that wall overlaps itself and defines portions of the balloon wall that are within a fold. A folded balloon has exposed portions of the folded balloon that are exposed to an exterior environment of the balloon, and unexposed portions that are not exposed because those portions are contained within a fold of the folded balloon.

Note that, although it is not shown in the drawings, it is possible to provide the outside surface of the balloon with various helical grooves that cross each other.

What is claimed is:

1. A balloon catheter comprising:
    a catheter tube disposed on a longitudinal axis; and
    an inflatable balloon having opposite ends and an outside surface having a first portion and a second portion, the ends of the balloon attached to the catheter tube,
    wherein in an uninflated and folded state, the first portion of the outside surface that is exposed to an exterior environment when the balloon is folded consists of a groove, which is substantially disappeared when the balloon is in an inflated state at an intended operating pressure during use, and the second portion of the outside surface that is within a fold of the balloon and not exposed to the exterior environment does not have the groove, and
    wherein the groove fully extends from one end to another end of the opposite ends of the balloon and only over the outside surface that is exposed when the balloon is folded.

2. The balloon catheter according to claim 1, whereby the groove fully extends at least transversely in a longitudinal direction of the balloon.

3. The balloon catheter according to claim 2, whereby the groove fully extends at a predetermined angle with regard to the longitudinal direction of the balloon.

4. The balloon catheter according to claim 2, whereby the groove extends helically from the one end to the another end of the balloon.

5. The balloon catheter according to claim 4, further including another groove that fully extends helically from the one end to the another end of the balloon and cross each other.

6. The balloon catheter of claim 1, wherein the balloon includes a first section at one end having a first radial dimension less than a second radial dimension of a second section of the balloon in an inflated state, wherein the groove extends along both the first section and the second section in the uninflated and folded state.

7. The balloon catheter of claim 1, wherein the balloon includes a frusto-conical portion adjacent each end, and wherein the groove extends at least partially along the frusto-conical portion in the uninflated and folded state.

8. A catheter, comprising:
    a catheter shaft disposed on a longitudinal axis; and
    a balloon mounted on the catheter shaft, the balloon disposed on the shaft and having a continuous balloon wall that is circumferentially folded upon itself about the axis, portions of the folded balloon wall that are exposed to an exterior environment being a first portion of the balloon wall and portions of the folded balloon wall that are not exposed to the exterior environment being a second portion of the balloon wall, said balloon wall consisting of a plurality of grooves disposed on the first portion of the balloon wall and not disposed on the second portion of the balloon wall, each of the plurality of grooves disposed to align with an adjacent one of the plurality of grooves and each of the plurality of grooves substantially disappeared when the balloon is in an inflated state at an intended operating pressure during use, and
    wherein the plurality of grooves remain unoccupied.

9. The catheter of claim 8, the balloon having a plurality of circumferential folds.

10. The catheter of claim 8, the plurality of aligned grooves are disposed to join together to form a substantially continuous groove extending circumferentially about the axis on the first portion of the balloon wall when the balloon is in an uninflated and folded state.

11. The catheter of claim 8, the plurality of aligned grooves are disposed to join together to form first and second substantially continuous grooves extending circumferentially about the axis on the first portion of the balloon wall when the balloon is in an uninflated and folded state.

12. The catheter of claim 11, the first and second substantially continuous grooves intersecting each other.

13. The balloon of claim 8, wherein the plurality of grooves fully extend from a first end of the balloon to a second, opposite end of the balloon.

* * * * *